(12) United States Patent
Jammet et al.

(10) Patent No.: US 6,626,904 B1
(45) Date of Patent: Sep. 30, 2003

(54) IMPLANTABLE INTERVERTEBRAL CONNECTION DEVICE

(75) Inventors: Jean Jammet, Objat (FR); Jean-Pierre Lenfant, Rochechouart (FR); André Peyre, Bordeaux (FR); David Jammet, Objat (FR)

(73) Assignees: Societe Etudes et Developpements - SED, Objat (FR); Societe Multi-Poles Conseils, Rochechouart (FR)

( * ) Notice: Subject to any disclaimer, the term of this patent is extended or adjusted under 35 U.S.C. 154(b) by 108 days.

(21) Appl. No.: 09/627,128

(22) Filed: Jul. 27, 2000

(30) Foreign Application Priority Data

Jul. 27, 1999 (FR) .............................................. 99 09981

(51) Int. Cl.[7] .............................................. A61B 17/56
(52) U.S. Cl. ...................................................... 606/61
(58) Field of Search ............................... 606/59, 60, 61

(56) References Cited

U.S. PATENT DOCUMENTS

| | | | | |
|---|---|---|---|---|
| 5,084,048 A | * | 1/1992 | Jacob et al. ................... | 606/61 |
| 5,196,013 A | | 3/1993 | Harms et al. .................. | 606/61 |
| 5,330,474 A | * | 7/1994 | Lin .............................. | 606/61 |
| 5,468,241 A | | 11/1995 | Metz-Stavenhagen et al. . | 606/61 |
| 5,613,968 A | * | 3/1997 | Lin .............................. | 606/61 |
| 5,735,851 A | * | 4/1998 | Errico et al. ................... | 606/61 |
| 5,961,516 A | * | 10/1999 | Graf ............................. | 606/61 |
| 6,083,226 A | * | 7/2000 | Fiz ............................... | 606/61 |
| 6,187,005 B1 | * | 2/2001 | Brace et al. ................... | 606/61 |
| 6,273,914 B1 | * | 8/2001 | Papas ....................... | 623/17.11 |

FOREIGN PATENT DOCUMENTS

| | | |
|---|---|---|
| DE | 3841008 A1 | 6/1990 |
| DE | 90 04 960.8 | 10/1991 |
| FR | 2 697 428 | 5/1994 |

* cited by examiner

*Primary Examiner*—John J. Wilson
(74) *Attorney, Agent, or Firm*—Young & Thompson

(57) ABSTRACT

The object of the invention is an implantable intervertebral connection device comprising at least two pedicular screws (1, 2) provided in their upper portion with a hexagonal head (3) prolonged by a cylindrical bearing (4, 4') and an inter-screw connection of adjustable length anchored at each end on said bearings, characterized in that said inter-screw connections constituted, on the one hand, by a ball (7, 7') preferably of a resiliently deformable material threaded on each bearing (4) and, on the other hand, by two connection elements (E1, E2; E'1, E'2) in prolongation of each other and interconnected by a screw system (17, 18; 18', 41, 42) for adjustment of spacing, the free ends of the elements being shaped as a cup (8, 9; 8', 9') which is concave and threadable on said bearing (4, 4') and matching said ball (7, 7') such that in line with each pedicular screw (1, 2; 1', 2') the ball will be sandwiched between two cups (8, 9; 8', 9') of two connections associated with the screw, means (6, 6') being provided to bring together toward each other the two cups (8, 9; 8', 9') by gripping said ball (7, 7') and securing the assembly of the pedicular screw.

Use in treatment of the vertebral column.

17 Claims, 6 Drawing Sheets

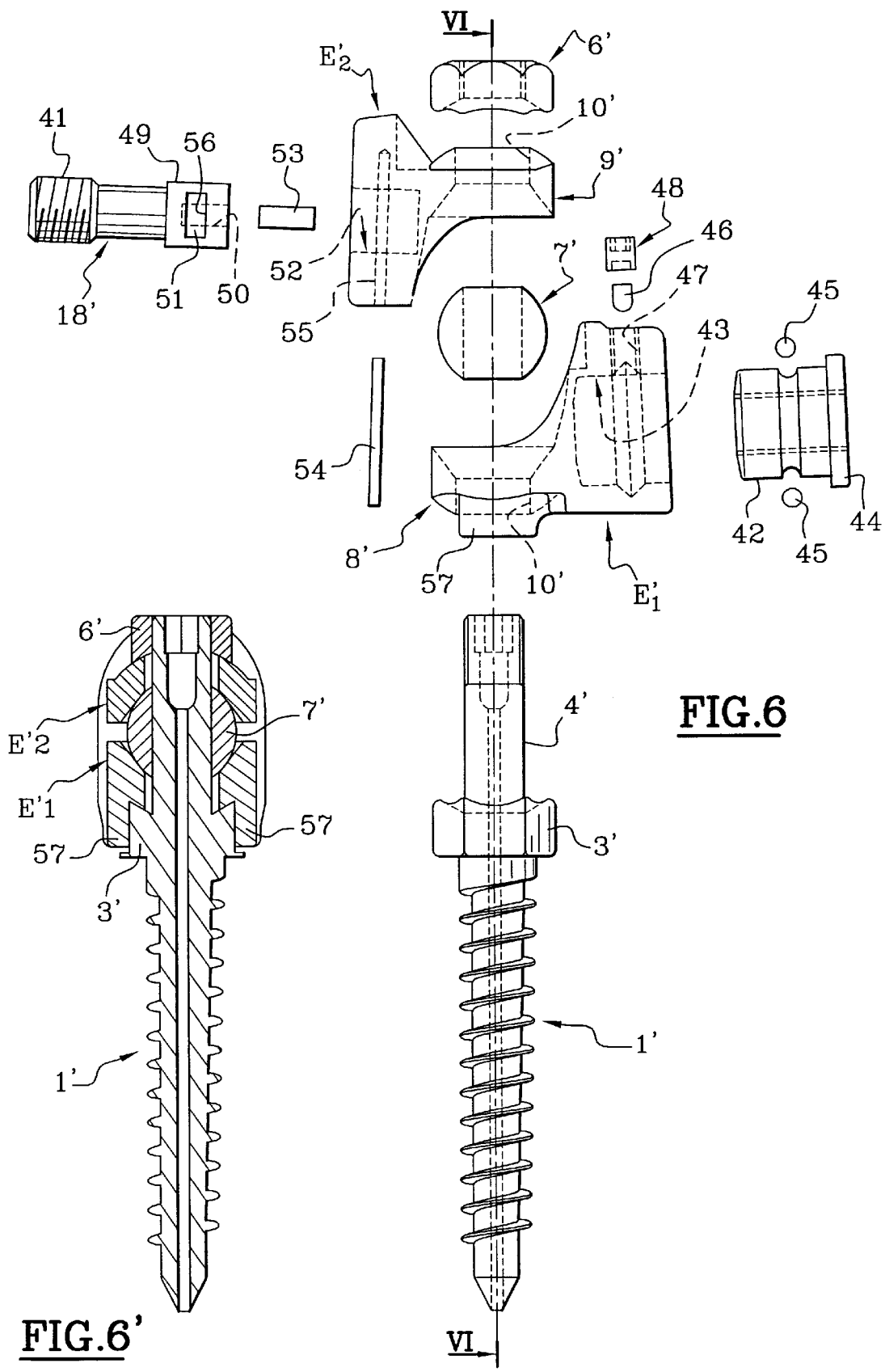

IMPLANTABLE INTERVERTEBRAL CONNECTION DEVICE

FIELD OF THE INVENTION

The present invention relates to an implantable intervertebral connection device, more particularly adapted to secure together two or more vertebrae.

The invention seeks to replace and maintain according to an arrangement as close as possible to normal, the displaced or deficient vertebrae, particularly in the treatment of certain cases of soliosis, cyphosis, exaggerated lordosis, vertebral instability or substantial decrease of the intervertebral space from whatever the cause.

BACKGROUND OF THE INVENTION

From FR 2 698 533 is known an implantable intervertebral connection device permitting two by two connection of several vertebrae with the aid of pedicular screws prolonged by a cylindrical bearing on which is screwed a spherical ferrule of an inter-screw connection element provided with at its other end either with a spherical ferrule or with a spherical-concave cup coacting with a spherical ferrule of a second connection on a same pedicular screw.

The connection element is of the type with a chain and the securement of the assembly is ensured by nuts engaged on the cylindrical bearing ends and pressed against each ferrule or each ferrule-cup assembly as the case may be, against a spherical seat provided on a hexagonal head of the pedicular screw.

If such a device permits adjustment of the intervertebral spacing, both in extension and retraction, by an action on the chain of each inter-screw connection, and if it also permits taking account of the non-parallelism of the axes of the pedicules in situ by an adjustment of the angle formed by the two connections from the same pedicular screw, thanks to the device with a ball ensuring the junction between the screw and the inter-screw connection elements, this intervertebral connection assembly nevertheless has serious drawbacks relating to its rigidity, preventing the patient particularly from flexion or rotation of the torso.

Moreover, the assembly of the components of the system being of metal such as for example titanium alloy, it is difficult to maintain sufficient gripping of the elements of the connection ball and often a posterior intervention for the emplacement of the intervertebral prosthesis will be necessary to reset the screws for blocking said balls.

SUMMARY OF THE INVENTION

The present invention seeks to overcome these various drawbacks by providing an implantable intervertebral connection device, adapted to permit not only adjustment of the intervertebral spacing and an adaptation to the angulation of the pedicules relative to each other, but also giving the patient improved comfort by a design of the device giving it suitable elasticity to permit movements of flexure, rotation of the torso and absorbing shocks.

To this end, the invention has for its object an implantable intervertebral connection device comprising at least two pedicular screws provided in their upper portion with a hexagonal head prolonged by a cylindrical bearing and an inter-screw connection of adjustable length, anchored to each end of said bearings, characterized in that said inter-screw connection is constituted on the one hand by a ball threaded on each bearing and, on the other hand, of two connection elements in prolongation of each other and interconnected by a system of screws for adjusting the spacing, the free ends of the elements being shaped as a concave cup skewered on said bearing and matching said ball such that in line with each pedicular screw the ball will be held in sandwich fashion between two cups of two connections associated with the screw, means being provided to move the two cups toward each other to grip said ball and to secure the assembly of the pedicular screw.

Preferably, the ball is of a resiliently deformable material.

The resilient nature of the rotary junction at the level of each pedicular screw permits absorbing the shocks and better distribution of forces along the prosthesis.

The latter not being constituted by a rigid chain but by a string of elements or links all adapted to have at their ends a certain resilient clearance in all directions, including axially of the pedicular screws, the patient thus has the possibility of moving his torso in flexure and rotation relative to the pelvis, of a certain amplitude, by thus outfitting the spine.

Preferably, the screw system connecting the two elements of an inter-screw connection is constituted by a tapped sleeve secured to one of the elements and a coacting screw-threaded rod, connected to the other element by means of a resilient abutment blockage system.

According to a modified embodiment, the screw system connecting the two elements of an inter-screw connection is constituted by a rod provided at one end with a screw-threaded head engaged in a tapping of a sleeve received in one of the above elements and at its other end, with a cylindrical head received in the other of the elements, means being provided, on the one hand, to permit either the free rotation or the blockage in rotation of said sleeve in the carrying element and, on the other hand, to retain and block in rotation said cylindrical head in the carrying element, a resilient abutment being provided between the head and the element.

Such a device not only permits the adjustment of the intervertebral spacing, not only in extension but also in retraction, but ensures a shock-absorbing connection between the two elements of the connection whilst blocking in rotation the screw portion, thereby guaranteeing the desired spacing.

At the two ends of the intervertebral connection device, the containing-gripping means for the ball of the two end pedicular screws can be lightened, because there is no connection with anything else, by providing the sandwiching of the balls in question between the cup of the single connecting element and a simple cup serving as a washer interposed between the ball and the hexagonal head of the pedicular screw or the blocking nut of the assembly, as the case may be.

Or course the cups have a passage hole for the cylindrical bearing of the pedicular screws of a diameter substantially greater than that of said bearing, so as to impart to the cups a certain omnidirectional angular clearance, but the surfaces, respectively of the hexagonal head and of the blocking nut of the assembly, turned toward the ball, are configured in correspondence with the surface facing the cups.

The ball is preferably spherical, but could if desired have another suitable shape, however the surfaces of the cups turned toward the ball are either spherical or truncated conical or else faceted.

BRIEF DESCRIPTION OF THE DRAWINGS

Other characteristics and advantages will become clear from the description which follows, of a preferred embodiment of the device of the invention, which description is given solely by way of example and with respect to the accompanying drawings, in which:

FIG. 6 is an exploded view of a modified embodiment of the connection device according to the invention;

FIG. 6' shows the assembly of FIG. 6 mounted, in cross-section on the line VI—VI;

DETAILED DESCRIPTION OF THE DRAWINGS

Figure 1:
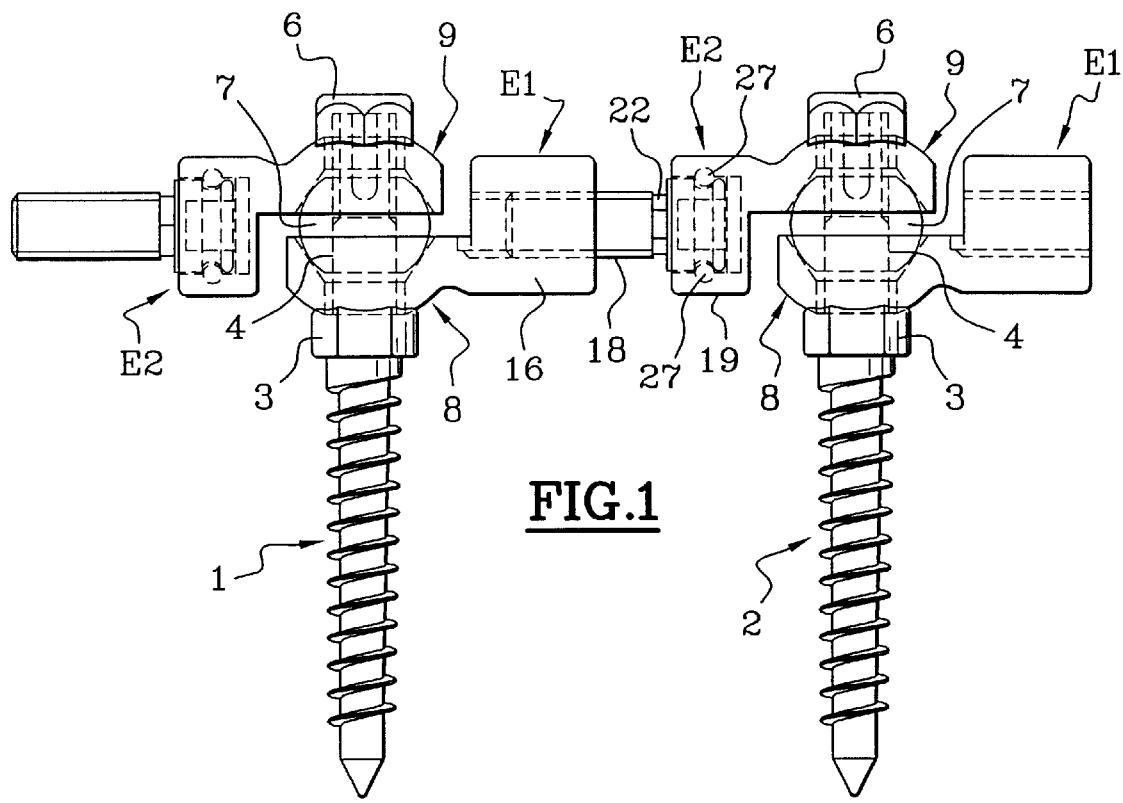
FIG. 1 is a side elevational view of a vertical connection device according to the invention.

In FIG. 1, there is shown the connection between two pedicular screws 1 and 2 by a device according to the invention.

The screws 1 and 2 comprise at their upper end a conventional hexagonal head 3 prolonged by a cylindrical bearing 4 screw-threaded at its end 5 (FIG. 2) so as to receive a nut 6 for blocking a ball 7 serving as a ball-bearing, itself held in sandwich fashion between a lower cup 8 and an upper cup 9, both provided at their center with a hole 10 of a diameter substantially greater than that of the cylindrical bearing 4, so as to permit free threading of the cups on the bearing as well as a certain radial clearance for the bearing.

The ball 7 is provided with a bore 11 of a diameter corresponding to that of the bearing 4 on which it is also freely threaded.

The ball is for example spherical and is preferably made of a resiliently compressible material, such as a plastic material, for example polyethylene or polyurethane.

Figure 2:
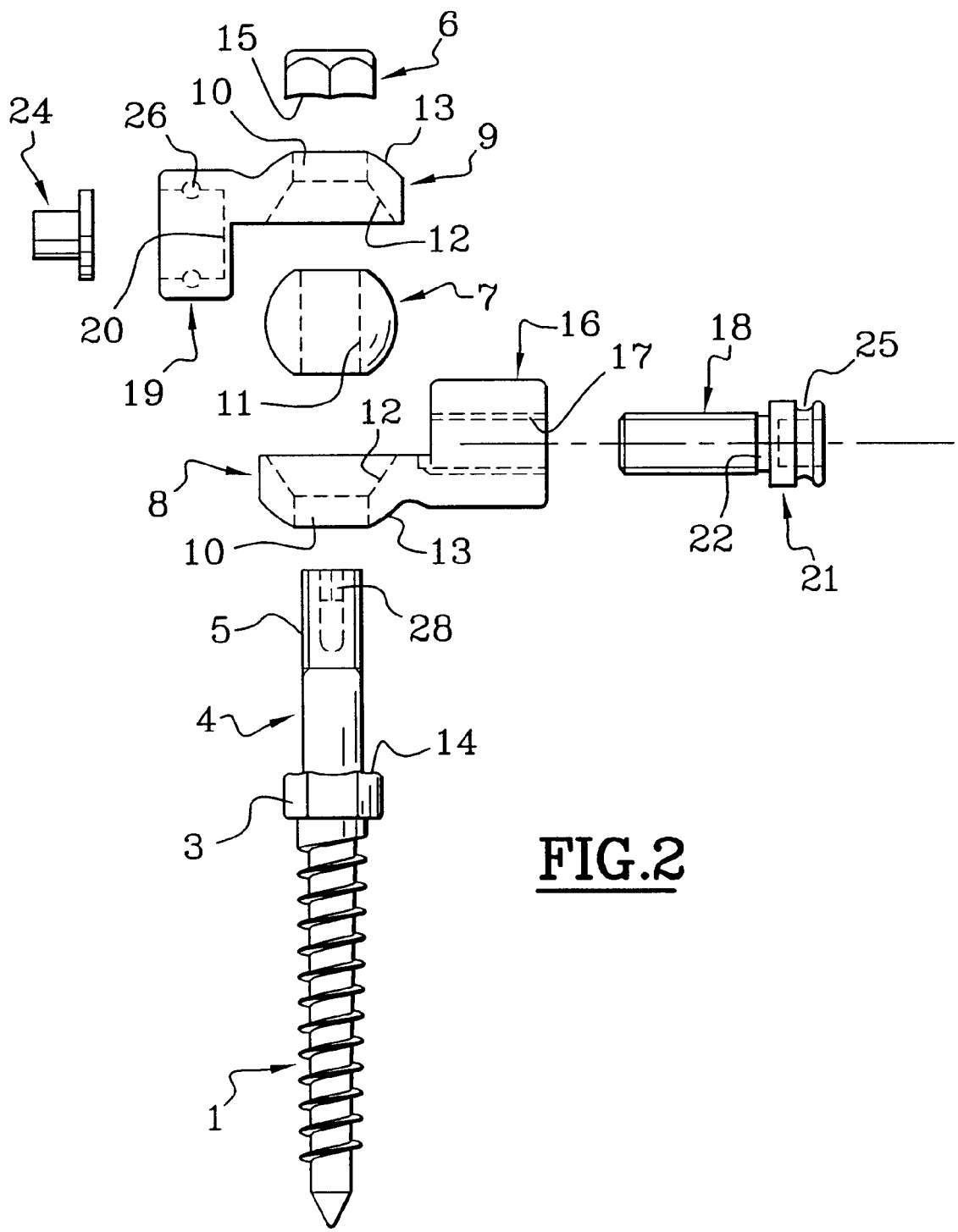
FIG. 2 is an exploded view of a pedicular screw of the device of FIG. 1, with its two connecting elements.

The cups 8 and 9 are of generally concave shape with a surface 12 turned toward the ball 7 of a spherical shape corresponding to the ball or of a truncated conical shape as shown in FIG. 2. If desired, the surface 12 can be faceted, with six or eight facets for example.

The external surface 13 of the cups is for example convex-spherical so as to match respectively one corresponding concave surface that is shaped either (14) on the hexagonal head 3, or (15) on the blocking nut 6.

Each of the two screws 1, 2 being connected to another pedicular screw comprises a lower cup 8 serving as a first connection with one screw and an upper cup 9 serving as a second connection with another screw.

Each inter-screw connection thus comprises two elements generally shown at E1 and E2 respectively, which can be brought together or spaced apart by a screw system ensuring their juncture in prolongation of each other.

To this end, the element E1 comprises a block 16 secured to the lower cup 8 laterally and provided with a tapped hole 17 adapted to receive a screw-threaded rod 18 secured to the element E2.

Figure 4:
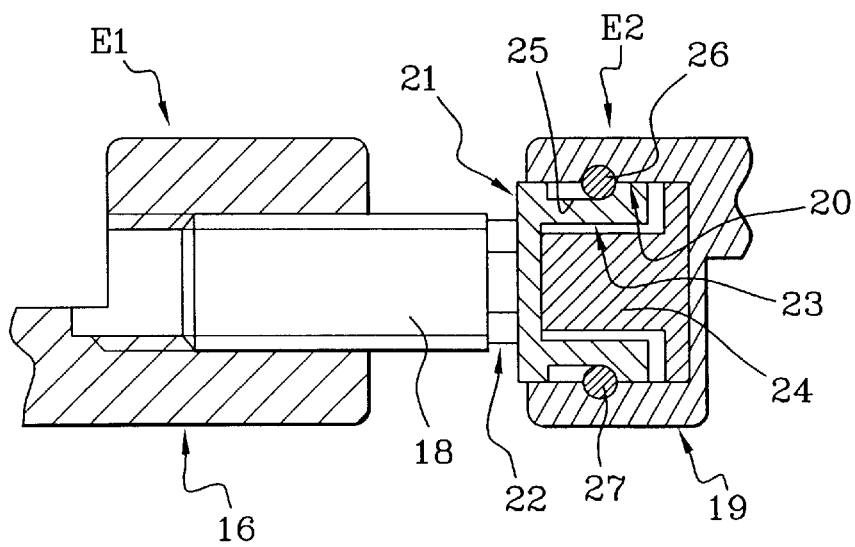
FIG. 4 is a fragmentary enlarged view of the connection between the two screws of FIG. 1.

The element E2 comprises a block 19 secured to the upper cup 9 laterally and provided with a cylindrical recess 20 (FIG. 4) adapted to receive a head 21 of generally cylindrical shape provided at the end of the screw-threaded rod 18.

Of course, the positions of the elements E1, E2 can be reversed, the cup 8 of the element E1 being adapted to be disposed in position with the upper cup and conversely for the cup 9 of the element E2.

The head 21 is connected to the screw-threaded rod 18 by an neck 22 of hexagonal cross-section to permit rotation of the screw 18.

The head 21 is moreover hollow and comprises a cylindrical recess 23 opening axially in the direction of the bottom of the recess 20.

A buffer block 24 of resiliently compressible material, for example of the same material as the ball 7, is received in the recess 20 and occupies the recess 23 of the head 21.

The outer peripheral surface of the head 21 is provided with a circular throat 25, however the block 19 is laterally pierced (FIG. 3) with two parallel blind holes 26, at the height of the wall of the recess 20, so as to receive therein two pins 27 for blocking the head 21.

The head 21 is engaged in the recess 20 and compresses the resilient block 24.

When the throat 25 arrives at the height of the holes 26, which is controlled by the rear surface of the head 21 coming flush with the forward surface of the block 19, the pins 27 are inserted in the holes 26 and penetrate the throat 25, on opposite sides of the head 21. This latter is thus retained trapped and is braked as to rotation because of the resilient pressure of the buffer block 24.

It is to be noted that the connection E1, E2 can thus resiliently receive the axial compression and shocks, absorbed by the block 24.

Figure 3:
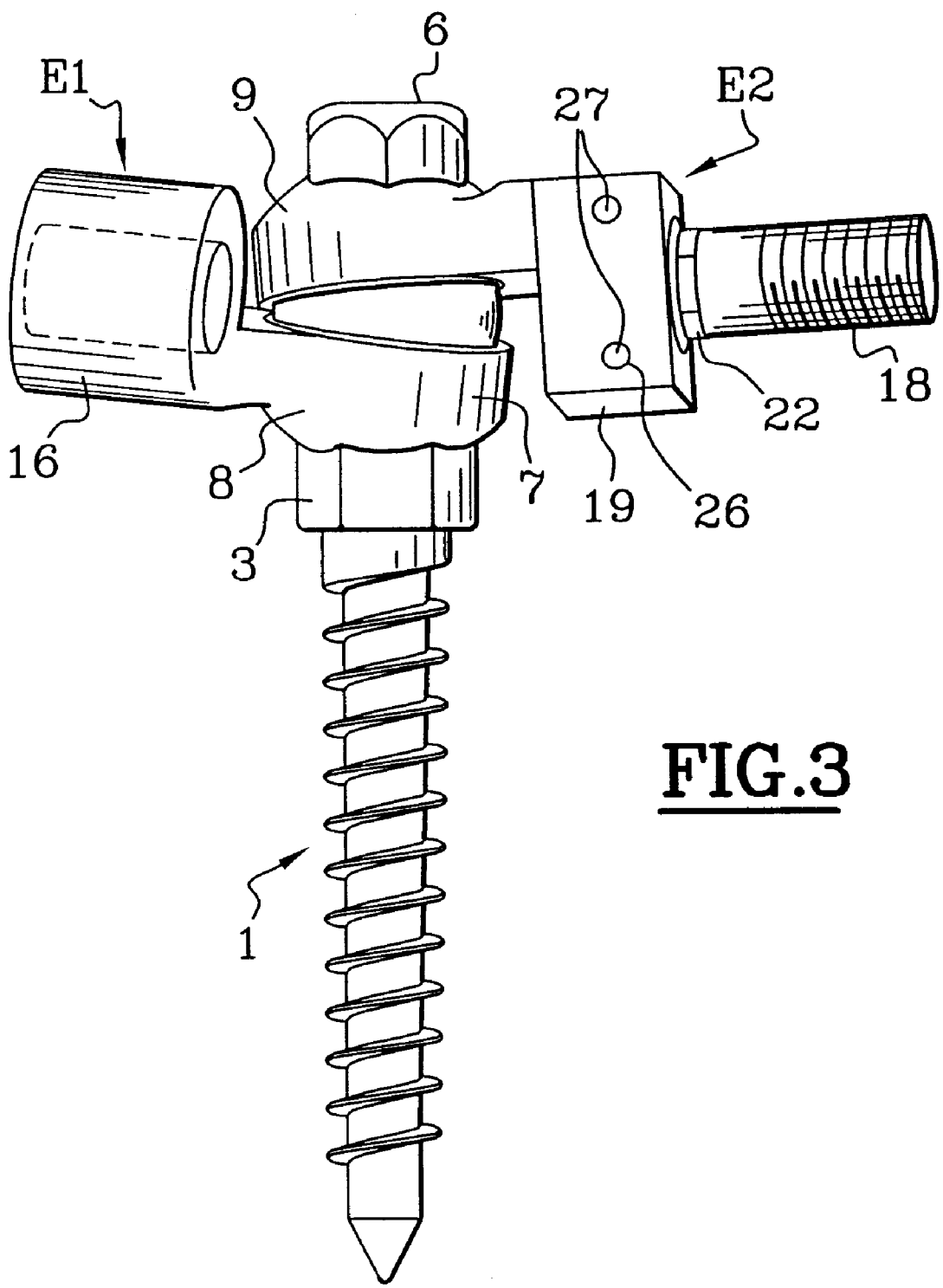
FIG. 3 shows the possibilities of angular clearance of a device of the type of FIG. 2, once mounted.

As can be seen in FIG. 3, the ball connection provided by the ball 7 trapped in sandwich fashion between the lower cup 8 and the upper cup 9, permits axial disalignment of the elements E1, E2 which can to a certain extent orient themselves independently in different directions by sliding of the ball 7 of the two opposite taps formed by the cups 8, 9, thanks to their diameter 10 substantially greater than that of the bearing 4 on which they are threaded.

When the elements E1, E2 are suitably oriented, with the appropriate intervertebral spacing, the nuts 6 are gripped and resiliently blocked, which prevents any later untimely unlocking.

The configuration of the surface 12 with the cups according to a truncated conical surface, or if desired faceted, facilitates the axial prepositioning of the cups as well as their emplacement during gripping of the nut 6.

The upper end of the pedicular screws 1, 2 is pierced with a blind hole in which is provided a hollow recess with six sides 28 (FIG. 2).

This impression 28 is accessible through the nut 6 by a suitable key so as to block in rotation the screw (1, 2) during gripping of the nut 6.

The intervertebral connection thus constituted resiliently absorbs shocks whilst having suitable rigidity, of sufficient flexibility to permit the patient various movements of the torso relative to the pelvis, such as flexure, rotation, which increases all the more the comfort of said patient.

Figure 5:
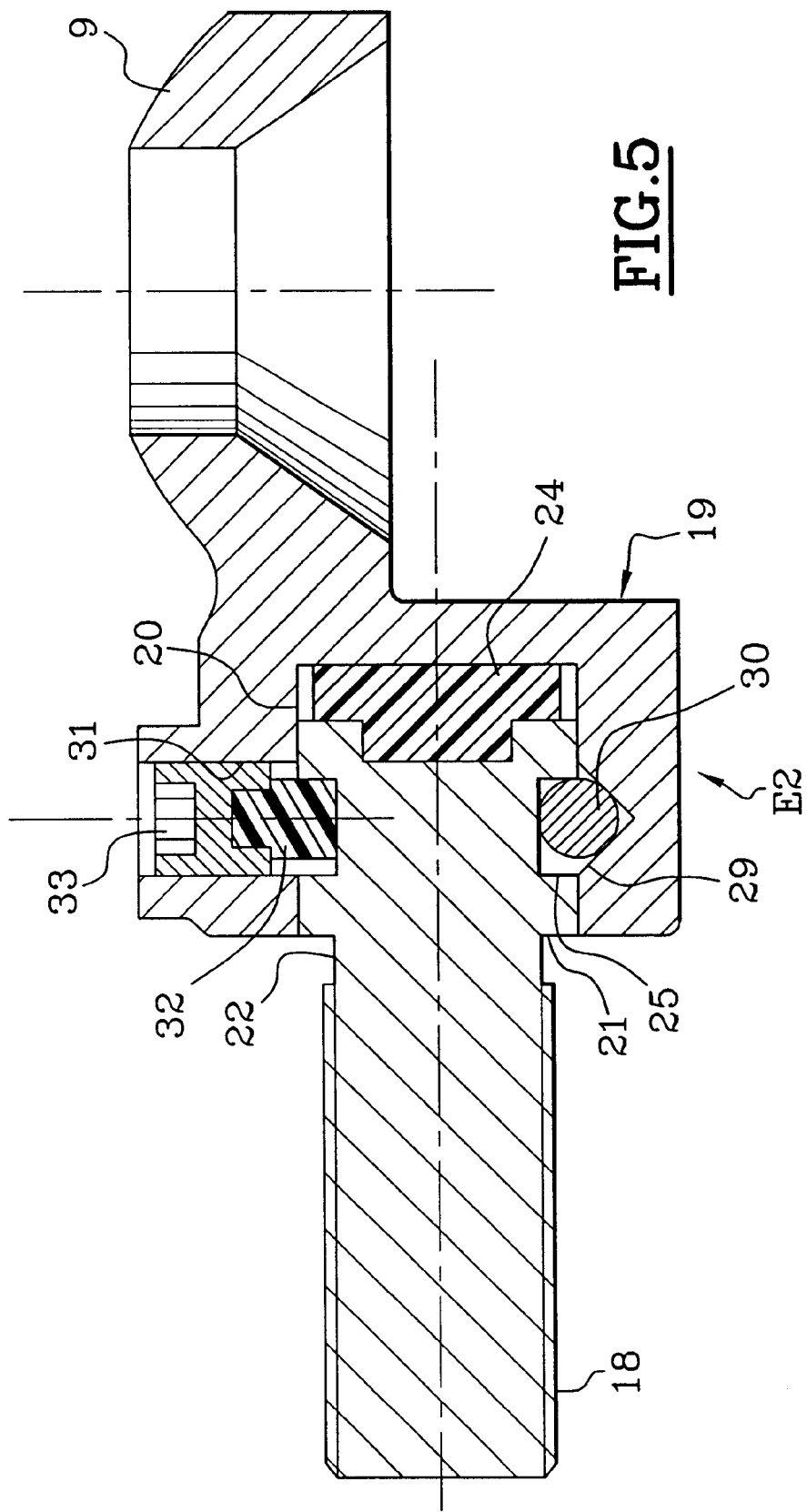
FIG. 5 is an axial cross-sectional view of a modified embodiment of connecting element.

FIG. 5 shows a modification of the resilient securement between the screw-threaded rod 18 and the element E2. According to this modification, the recess 20 of the block 19 is provided on its cylindrical wall with a circular throat 29 of V cross-section, adapted to receive blocking balls 30 disposed both in the throat 29 and in the annular throat 25 of the head 21, the resilient buffer block 24 being compressed.

The throat 29 is accessible from outside the block 19 by a screw-threaded bore 31 receiving a small block 32 of resilient material occupying the place of a ball 30 and pressed by a screw 33. When the head 21 is in the correctly seated position in the recess 20, the balls 30 are introduced through the bore 31 into the annular space 25–29, then the bore is closed by elements 32, 33. The screw 33 is gripped once the rod 18 is correctly positioned in its sleeve 16, to compress the block 32, thereby preventing effectively any ultimate untimely rotation of the rod 18 in its sleeve 16.

At the two ends of the intervertebral connection device, the containing-compressing means for the ball of the two end pedicular screws can be lightened, because there is no other connection, by providing the sandwich grip of the balls in question between the cup of the single connection element and a simple cup serving as a washer interposed between the ball and the hexagonal head of the pedicular screw or the blocking nut of the assembly, as the case may be.

This simple cup is identical to the cups 8, 9 except that it is not attached as these latter to the elements 16, 19.

Figure 7:
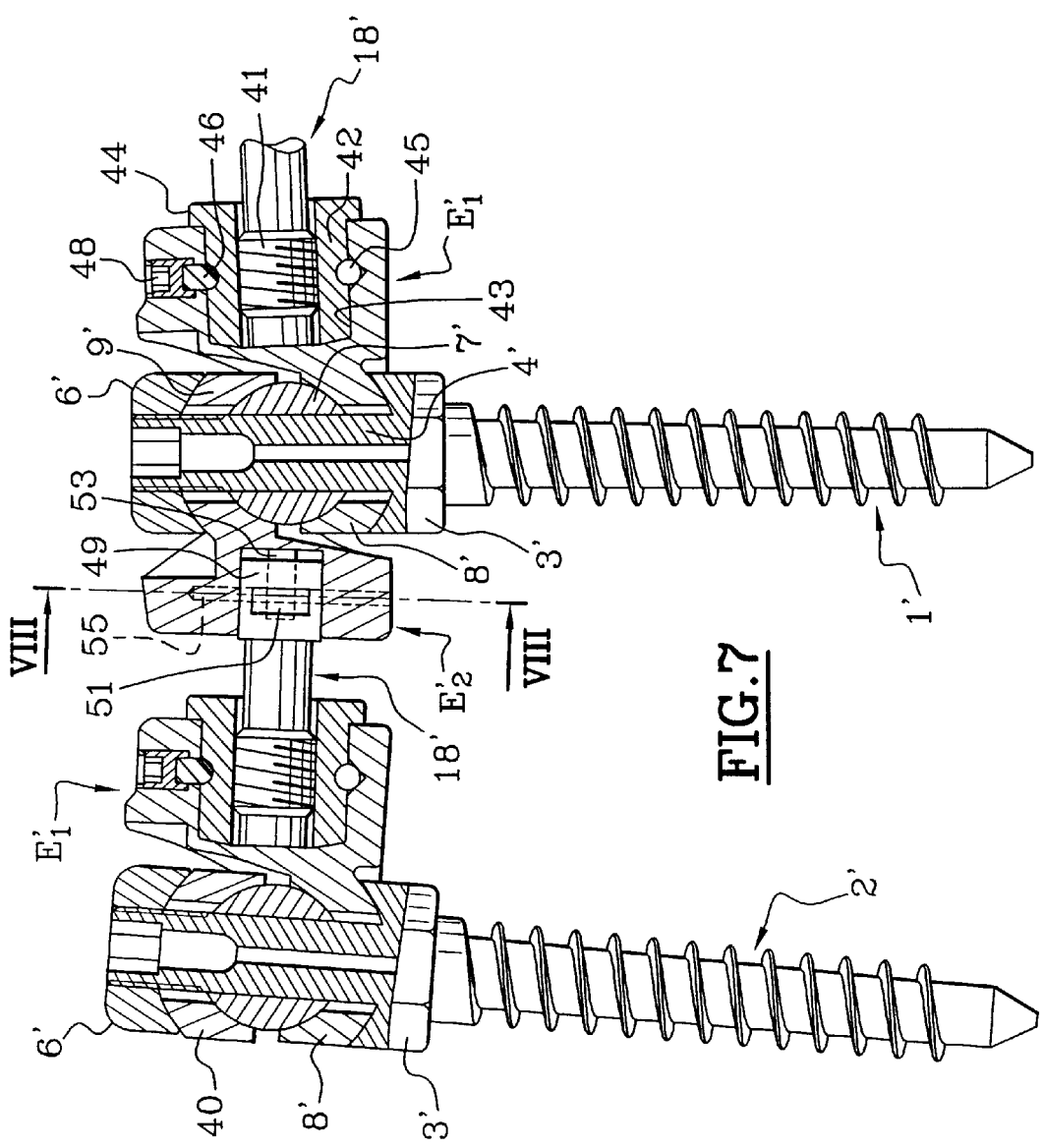
FIG. 7 shows the end of a connection device using the modification of FIG. 6.

Such simple cup is shown at 40 in FIG. 7, which shows a modified embodiment of the invention of which an exploded view is given in FIG. 6.

In this modification, the pedicular screws 1', 2', hexagonal heads 3', bearings 4', balls 7', blocking nuts 6', lower cup 8' and upper cup 9', passage holes 10', are substantially identical to the homologous elements of the embodiment of FIG. 1.

Only the inter-screw connection device E'1 and E'2 and the junction rod 18' differ slightly from their homologs in said FIG. 1.

Thus, the screw-threaded end 41 of the rod 18' is engaged in a tapping of a sleeve 42 introduced into a blind hole 43 provided in the element E'1.

The sleeve 42 is provided with an end collar 44 which is faceted and is retained trapped in the recess 43, whilst being adapted to pivot about its axis, thanks to a set of balls 45 engaged in two circular channels provided facing the walls of the sleeve 42 and of the hole 43, respectively.

The blockage in rotation on itself of the sleeve 42 can be obtained with a small block 46 of resilient material inserted between two balls 45 and introduced through a lateral hole 47 in the element E'1. This same hole 47 is tapped to receive a screw 48 for pressing the resilient block 46 against the sleeve 42, thereby preventing its rotation.

At its other end, the rod 18' comprises an enlarged cylindrical head 49 provided on the one hand with a blind hole 50 on its end surface and on the other hand with two parallel lateral flats 51.

The head 49 is adapted to engage freely in a blind hole 25 provided in the other element E'2 while compressing a small cylindrical block 53 of resilient material, introduced previously into the hole 50 and interposed between the bottoms of the two blind holes 50, 52.

Figure 8:
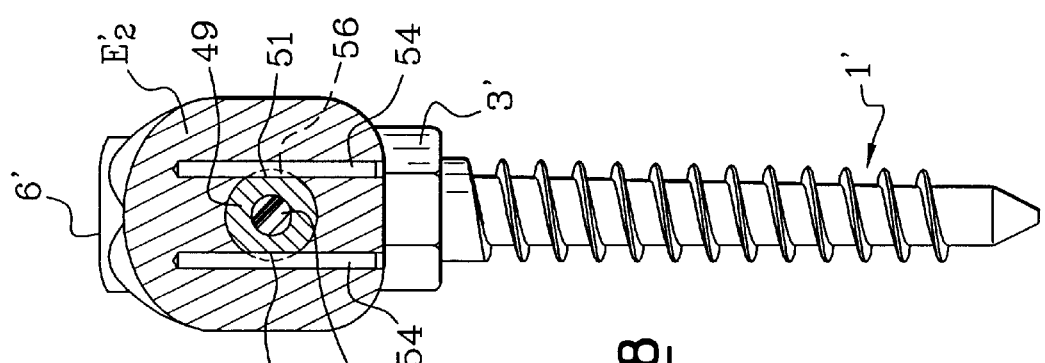
FIG. 8 is a cross-sectional view on the line VIII—VIII of the device of FIG. 7.

The rotation about its axis of the rod 18' is prevented with the help of two pins 54 engaged in two parallel holes 55 of the element E'2 (FIG. 8) by being trapped in the hole 52 and by engaging themselves in the spaces left by the flats 51.

The rod 18' which is pressed by the compressed block 53 is retained by the pins 54 in contact with the sides 56 (FIGS. 6 and 8) of the cutouts defining the flats 51.

The spacing between the elements E'1, E'2 is adjusted by turning, with the help of a flat key for example, the hexagonal collar 44 of the sleeve 42, after unlocking the screw 48 of course. The rotation of the sleeve 42 gives rise to axial displacement of the rod 18' in the sleeve 42, because the rotation of the rod is prevented by the flats 51 and the pins 54. Moreover, the rod 18' is constantly in resilient abutment against the bottom of the hole 52, which ensures a certain axial clearance of the rod relative to the element E'2, no matter what the spacing between the elements E'1, E'2.

It is also to be noted that the element E'1 (FIG. 6) is provided in its lower portion with two flat elongations 57 facing each other and adapted, during mounting of the device (FIG. 6'), to position themselves against two opposite facets of the hexagonal head 3', thereby mutually immobilizing in rotation the pedicular screw 1' and the inter-screw connection (E'1, 18').

Finally, the invention is obviously not limited to the embodiments shown and described above, but covers on the contrary all modifications, particularly as to the nature, shape and dimensions of the resiliently recompressible elements (7, 7', 24, 32). The shapes and dimensions of the cups 8, 8', 9, 9', as well as the nature of the resilient interconnection between rod 18, 18' and its carrying element E2, E'2 and the means for adjusting the spacing between the elements E1, E'1, E2, E'2.

It is particularly to be noted that according to its use, the balls 7, 7' could be if desired of a rigid material.

What is claimed is:

1. Implantable intervertebral connection device comprising at least two pedicular screws (1, 2; 1', 2') provided in their upper portion with a hexagonal head (3, 3') surmounted by a cylindrical bearing (4, 4') and an inter-screw connection of adjustable length anchored at each end to said bearings, said inter-screw connection being constituted by a ball (7, 7') engaged on each bearing (4) and by two connection elements (E1, E2; E'1, E'2) in prolongation of each other and interconnected by a screw system (17, 18; 18', 41, 42) for the adjustment of spacing, both free ends of each element being shaped as concave cups (8, 9; 8', 9') engaged on said bearing (4, 4') and mating with said ball (7, 7') such that in line with each pedicular screw (1, 2; 1', 2') the ball will be held in sandwich fashion between two said cups (8, 9; 8', 9') of two connections associated with the screw, means (6, 6') being provided to bring together the two cups (8, 9; 8', 9') by gripping said ball (7, 7') and securing together the assembly of the pedicular screw.

2. Device according to claim 1, characterized in that the ball (7, 7') is of a resiliently deformable material.

3. Device according to claim 1, characterized in that said screw system connecting the two elements (E1, E2) of one inter-screw connection is constituted by a tapped sleeve (16) secured to one of the elements and by a coacting screw-threaded rod (18), connected to the other element by means of a system of blocking with a resilient abutment (24).

4. Device according to claim 3, characterized in that said rod (18, 18') has a head (21, 49) in resilient abutment against a recess (20, 52) of said element (E2, E'2), means being provided to retain and block in rotation said head (21, 49) in said recess (20, 52).

5. Device according to claim 4, characterized in that said retaining-blocking means of the head (21, 49) are constituted by pins (29, 54) for retaining said head (21, 49) in a position of compression by a block (24, 53) of a resiliently compressible material disposed in said recess (20, 52).

6. Device according to claim 4, characterized in that said retaining-blocking means of the head (21) are constituted by a set of balls (30) interposed between the head (21) and its recess (20) and retaining the head in a position for compression of a block (24) of a resiliently compressible material disposed in said recess (20), a blockage in rotation of said head (21) being nevertheless ensured by a lateral screw (33) having a block (32) of resiliently compressible material against said head (21).

7. Device according to claim 4, characterized in that said retaining-blocking means of the cylindrical head (49) are constituted by a set of pins (54) coacting with flats (51) provided on said head (29) so as to block in rotation said rod (18').

8. Device according to claim 3, characterized in that between the screw-threaded rod (18) and the head (21) is provided a hexagonal section (22) to ensure the rotation of the screw-threaded rod (18) in its sleeve (16).

9. Device according to claim 1, characterized in that said screw system connecting the two elements (E'1, E'2) of an inter-screw connection is constituted by a rod (18') provided at one end with a screw-threaded head (41) engaged in a sleeve (42) received in one (E'1) of the two above elements and at its other end with a cylindrical head (49) received in the other (E'2) of the elements, means being provided, on the one hand, to permit either the free rotation or the blockage in rotation of said sleeve (42) in the carrying element (E'1) and, on the other hand, to retain in blocking rotation said cylindrical head (49) in the carrying element (E'2), a resilient abutment (53) being provided between the head and the carrying element.

10. Device according to claim 9, characterized in that said sleeve (42) has an external collar (45) permitting the rotation of the sleeve in its recess (43).

11. Device according to claim 1, characterized in that said cups (8, 9; 8', 9') have a hole (10, 10') for passage of the cylindrical bearing (4, 4') of the pedicular screws (1, 2; 1', 2'), of a diameter substantially greater than that of said bearing.

12. Device according to claim 1, characterized in that said means to bring together the cups (8, 9; 8', 9') and to secure the assembly of the pedicular screw (1, 2; 1', 2') are constituted by a blocking nut (6, 6') screwed on the screw-threaded end (5) of said bearing (4, 4').

13. Device according to claim 12, characterized in that the respective surfaces (14, 15) of a hexagonal head (3, 3') and of the nut (6, 6') for blocking the assembly, turn toward the ball (7, 7'), are shaped in correspondence with the facing surface of the cups (8, 9; 8', 9').

14. Device according to claim 1, characterized in that the ball (7; 7') is spherical.

15. Device according to claim 1, characterized in that the surface (12) of the cups (8, 9; 8', 9') turn toward the ball (7, 7') have a spherical, truncated conical or faceted surface.

16. Device according to one claim 1, characterized in that the connection element (E'1) turned toward the hexagonal head (3') of the pedicular screw (1') comprises two lower prolongations (57) facing each other and adapted to coact with said hexagonal head (3') to immobilize in rotation the latter.

17. Device according to one claim 1, characterized in that at the level of the two end pedicular screws of the intervertebral connection, the gripping of the ball (7') is ensured between the cup (8') of the end connection element (E'2) and a simple cup (40) serving as a washer interposed between the ball and the hexagonal head (3') of the screw or blocking screw (6') of the screw assembly.

* * * * *